United States Patent
Presura et al.

(10) Patent No.: US 7,925,056 B2
(45) Date of Patent: Apr. 12, 2011

(54) OPTICAL SPECKLE PATTERN INVESTIGATION

(75) Inventors: Cristian Presura, Eindhoven (NL); Coen Theodorus Hubertus Fransiscus Liedenbaum, Eindhoven (NL); Antonius Hermanus Maria Akkermans, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 921 days.

(21) Appl. No.: 11/815,451

(22) PCT Filed: Feb. 3, 2006

(86) PCT No.: PCT/IB2006/050369
§ 371 (c)(1),
(2), (4) Date: Aug. 3, 2007

(87) PCT Pub. No.: WO2006/085252
PCT Pub. Date: Aug. 17, 2006

(65) Prior Publication Data
US 2008/0146952 A1    Jun. 19, 2008

(30) Foreign Application Priority Data
Feb. 8, 2005 (EP) .................. 05300098

(51) Int. Cl.
*G01P 3/36* (2006.01)
*G01B 11/02* (2006.01)
*A61B 13/00* (2006.01)

(52) U.S. Cl. .......... 382/115; 382/124; 356/28; 356/512; 600/458

(58) Field of Classification Search .......... 382/115–116, 382/124, 190, 209, 218; 356/71, 28, 511, 356/512, 338, 450, 496, 458, 457, 336, 337; 600/300, 443, 437, 458, 407, 454; 348/175, 348/E9.026; 128/916
See application file for complete search history.

(56) References Cited

U.S. PATENT DOCUMENTS

| | | | | |
|---|---|---|---|---|
| 4,414,684 A | * | 11/1983 | Blonder | 382/127 |
| 5,291,013 A | * | 3/1994 | Nafarrate et al. | 250/227.14 |
| 5,811,826 A | * | 9/1998 | Shirley | 250/559.29 |
| 6,584,214 B1 | | 6/2003 | Pappu et al. | |
| 6,638,224 B2 | * | 10/2003 | Ohtsuki et al. | 600/443 |
| 7,292,232 B2 | * | 11/2007 | Ranta et al. | 345/175 |
| 7,302,088 B2 | * | 11/2007 | Amano et al. | 382/124 |
| 2005/0053264 A1 | | 3/2005 | Amano et al. | |

FOREIGN PATENT DOCUMENTS

JP   02005190   1/1990

(Continued)

OTHER PUBLICATIONS

Wen Wuqi et al: "An Application of Correlation Dimension", Lasers and Electro-Optics, CLEO/Pacific RIM '99, The Pacific RIM Conference, vol. 4, pp. 1239-1240.

(Continued)

*Primary Examiner* — Sheela C Chawan

(57) ABSTRACT

A method for investigating and ascertaining pulse or heartbeat includes directing illuminating radiation to illuminate a body part such as a finger. The illuminating radiation is of a wavelength or wavelength band substantially in the blue light region of the light spectrum. Then, an optical speckle pattern of the illuminated body part resulting from the illumination of the body part is obtained and imaged. The optical speckle pattern is representative of the heartbeat and by correlation of frames extracted from the speckle pattern, the pulse or beat extent of the body part may be ascertained.

16 Claims, 5 Drawing Sheets

FOREIGN PATENT DOCUMENTS

| | | |
|---|---|---|
| JP | 09084776 | 3/1997 |
| JP | 11332838 | 12/1999 |
| WO | 03056502 A1 | 7/2003 |

OTHER PUBLICATIONS

J David Briers: "Laser Doppler, Speckle and Related Techniques", Physiol. Meas., 22, pp. R35-R66, 2001.

Marie Sandstrom: "Liveness Detection in Fingerprint", http://www.ep.liu.se/exjobb/isy/2004/3557/exjobb.pdf, pp. 69, 71, 81, 82.

German De Costa: "Optical Remote Sensing of Heartbeat", Optics Communications, vol. 117, No. 5-6, pp. 395-398, 1995.

Maltoni D et al: "Securing Fingerprint System", Handbook of Fingerprint Recognition, pp. 281-292, 2003, XP002356777.

\* cited by examiner

OPTICAL SPECKLE PATTERN INVESTIGATION

The present invention relates to optical speckle pattern investigation and analysis, and in particular to optical speckle investigation techniques for biometric or biosensor applications.

Biometric apparatus is increasingly being used to authenticate the identity of individuals for security purposes. For example fingerprint sensor apparatus is often used in banks, airports or for secure area access systems. There are potential risks in using security systems that rely solely on the use of checking on the physical relief pattern markings of fingerprints or other body parts, in that fake body parts (for example a fake finger with a fake fingerprint relief pattern may be used to fool such sensors).

In a first aspect of the invention an improved technique has been devised.

According to a first aspect the present invention provides an investigation system for investigating a body part, the investigation system comprising:
    an illuminating radiation delivery arrangement, for directing illuminating radiation to the body part;
    an image capture arrangement for capturing an optical speckle pattern image of the illuminated body part, resultant from the illumination of the body part;
    a processor to process image data from the image capture arrangement, wherein the image data is processed to compare the captured optical speckle pattern of the body part with a reference speckle pattern in order to attempt to ascertain identity for the owner of the body part.

According to a second aspect, the invention provides, a method for investigation of a body part in order to attempt to ascertain identity for the owner of the body part, the method comprising:
    directing illuminating radiation to illuminate the body part;
    imaging an optical speckle pattern of the illuminated body part, resultant from the illumination of the body part;
    processing optical speckle pattern image data to compare the captured optical speckle pattern of the body part with a reference speckle pattern in order to attempt to ascertain identity for the owner of the body part.

According to a further aspect, the invention provides a system for processing image data, wherein captured optical speckle pattern image data for light scattered from a body part under investigation is processed and compared with a reference speckle pattern in order to attempt to ascertain identity for the owner of the body part.

In one embodiment the system further includes means for capturing an image of a characteristic physical relief pattern on the surface of the body part (for example an image of a fingerprint) and processing image data from the captured physical relief pattern image to attempt to ascertain identity for the owner of the body part. The technique of the present invention is therefore capable of providing a 2 fold check confirming or denying the identity of the individual.

In one embodiment the system includes means for ascertaining a pulse exhibited by the body part in order to confirm that the owner of the body part is alive. With this in mind, it is preferred that the processor is arranged to process optical speckle pattern image data from the image capture arrangement to ascertain a pulse exhibited by the body part in order to confirm that the owner of the body part is alive.

The technique of the present invention is therefore capable of checking, not only that the body part conforms to the identity of the reference, but also that the body part seems to belong to a live individual.

It has been found that a particularly stable speckle pattern is imaged where light in the blue region of the spectrum is used and that when observing such a stable speckle pattern, heartbeat/pulse measurement can be most conveniently ascertained by processing the image data.

According to a further aspect, the present invention therefore provides a method for investigation or ascertaining a pulse or heartbeat, the method comprising:
    directing illuminating radiation to illuminate a body part, the illuminating radiation being of a wavelength or wavelength band substantially in the blue light region of the spectrum;
    imaging an optical speckle pattern of the illuminated body part, resultant from the illumination of the body part;
    processing optical speckle pattern image data to ascertain a pulse or beat extant for the body part.

Accordingly, the invention also provides an investigation system for investigating a body part, the investigation system comprising:
    an illuminating radiation delivery arrangement, for directing illuminating radiation to the body part the illuminating radiation being of a wavelength or wavelength band substantially in the blue region of the spectrum;
    an image capture arrangement for capturing an optical speckle pattern image of the illuminated body part, resultant from the illumination of the body part;
    a processor to process image data from the image capture arrangement, wherein the image data is processed to ascertain a pulse or beat extant for the body part.

In one embodiment the optical speckle pattern is imaged using a camera, and correlations between image data from captured temporally spaced image frames are processed in order to ascertain the pulse or heartbeat.

The invention will now be further described in a specific embodiment, by way of example only and with reference to the accompanying drawings, in which.

Optical speckle investigation techniques rely upon coherent light (typically from a laser source) being scattered off a matt or unpolished surface having a surface topography. The surface causes the coherent light to be scattered with random phase and direction, such that when the scattered light is viewed, a grainy composition of randomly shaped and positioned, bright and dark areas are seen. This speckle pattern is the result of the constructive and destructive interference among the scattered light rays.

In obtaining the speckle pattern from a body part, such as a finger, laser radiation from a laser is used to illuminate a selected area of the finger. The scattered light is then collected and imaged using an imager such as a charge-coupled device (CCD).

Figure 1:
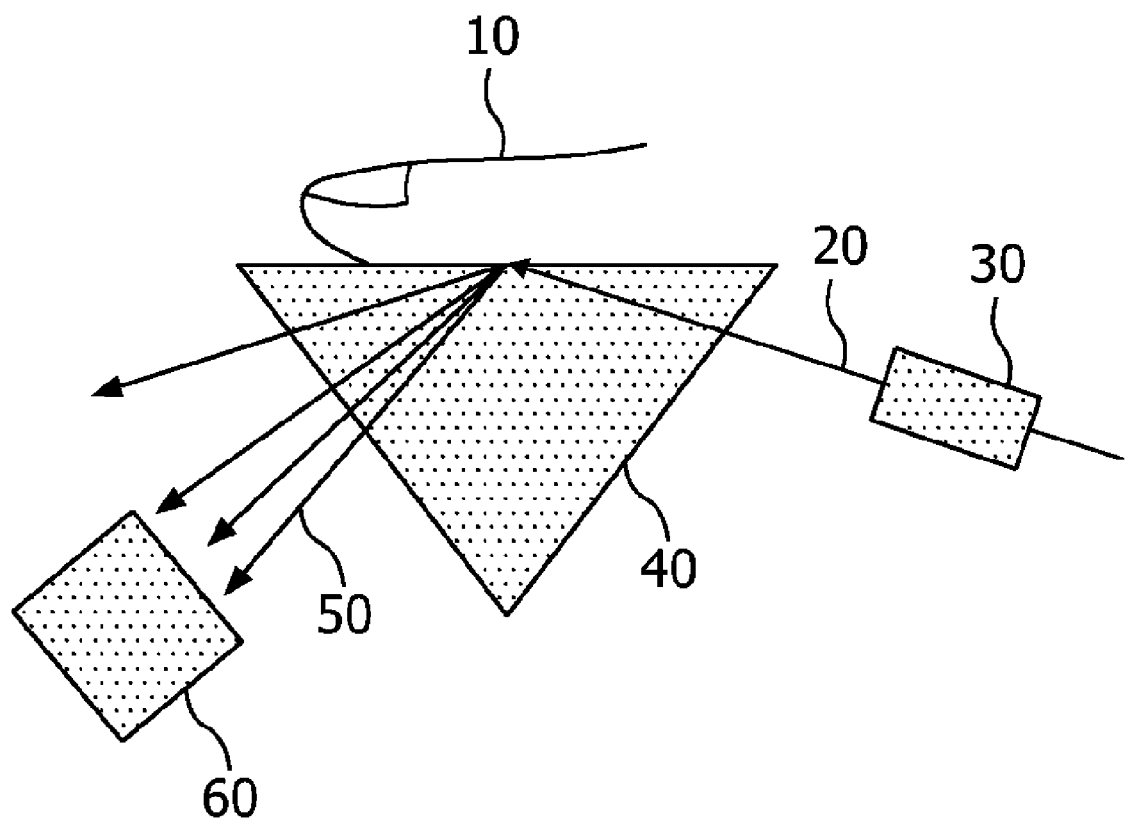
FIG. 1 is a schematic representation of the investigation system.

A typical investigation system, in accordance with this invention and as exemplified in a first embodiment, is shown in FIG. 1. A finger 10 is illuminated using coherent laser light 20 from a laser source 30. The finger is illuminated through a prism 40 in order to better separate the speckle forming rays 50 from the reflected ray, and the speckle pattern is viewed using a CCD imager 60.

Blue light has the shortest wavelength of the visible spectrum and accordingly can distinguish the finer detail of the finger. In addition, blue laser radiation as used in this process is found to provide the most stable speckle pattern. Accordingly, blue band laser light is the preferred illuminating radiation.

The body part under investigation, i.e. the finger 10, will emit infra-red (IR) radiation because of its inherent temperature. This IR radiation has a wavelength which is comparable to the red band of the visible spectrum. Consequently, if red light were used as the illuminating radiation, the CCD imager 60 would collect the emitted IR radiation in addition to the scattered speckle forming rays. This IR radiation would interfere with the scattered rays and thus de-stabilise the desired speckle pattern. As the CCD imager 60 is responsive to a wavelength range, an illuminating wavelength which is removed from the source of IR interference will produce the most stable pattern. Hence the use of blue illuminating radiation.

The speckle patterns obtained from directing the laser beam at various positions about the finger are found to be clear and have distinctive bright and dark spots. More importantly, the speckle patterns are found to be reproducible giving rise to its possible use as a biometric identification key.

Figure 2:
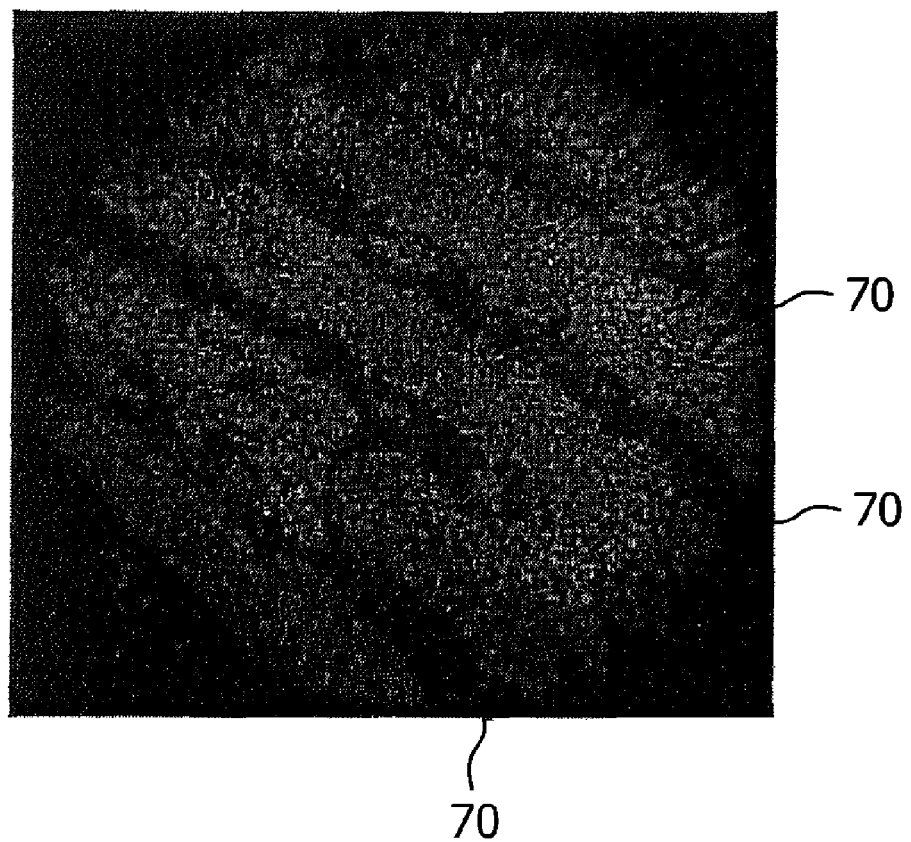
FIG. 2 is a focussed speckle pattern obtained from directing the laser beam at the fingerprint.

In accordance with this invention as exemplified in a second embodiment, the rays scattered from the surface of the fingerprint region of a finger can be focussed using a lens to image the relief of the fingerprint, in addition to the speckle pattern. Such an image is shown in FIG. 2. Clear striations 70 in the speckle pattern are evident and are indicative of the swirls and curves of the fingerprint. This speckle pattern can therefore be further used to identify the owner of the finger.

Finger movements can give rise to speckle changes which can lead to erroneous images with both identification techniques. However, this movement can be accommodated by cleaning the image using signal processing techniques such as Fourier analysis or by using an actuated laser source to follow the finger movement and thus minimise the effect.

The use of the speckle pattern obtained from a fingerprint is more beneficial than the fingerprint itself in identifying the identity of the finger. This is because the speckle pattern does not remain on the objects touched, as with the fingerprint. Consequently, it is impossible to copy the speckle pattern of the original finger without taking a measurement of the original finger.

It has been shown that it is possible to copy a fingerprint from an object previously touched and emboss the copy on an artificial finger to overcome fingerprint security systems. In addition to using the unique speckle pattern obtained from a finger and/or fingerprint using the investigation system of FIG. 1, the speckle pattern can also be used to overcome this security flaw with current fingerprint systems. This is achieved by monitoring the movement of the surface of the finger in order to establish a heartbeat and thus differentiate a "live" finger from an artificial finger.

Figure 3:
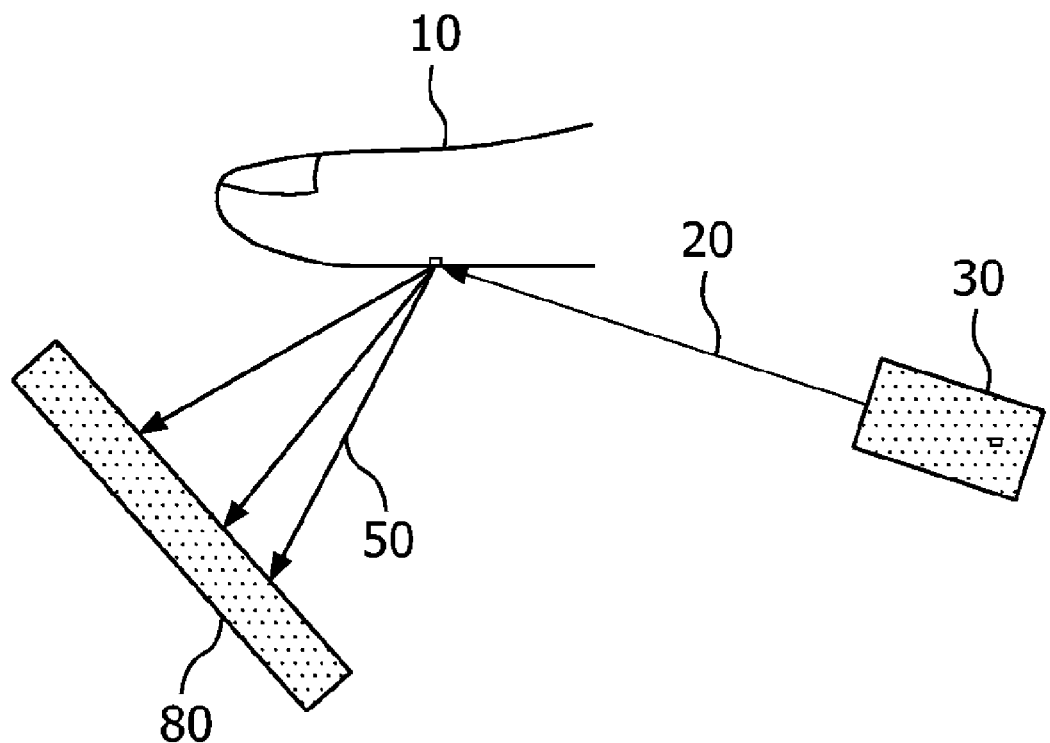
FIG. 3 is an alternative representation of the investigation system for ascertaining the heart beat.
Figure 4:
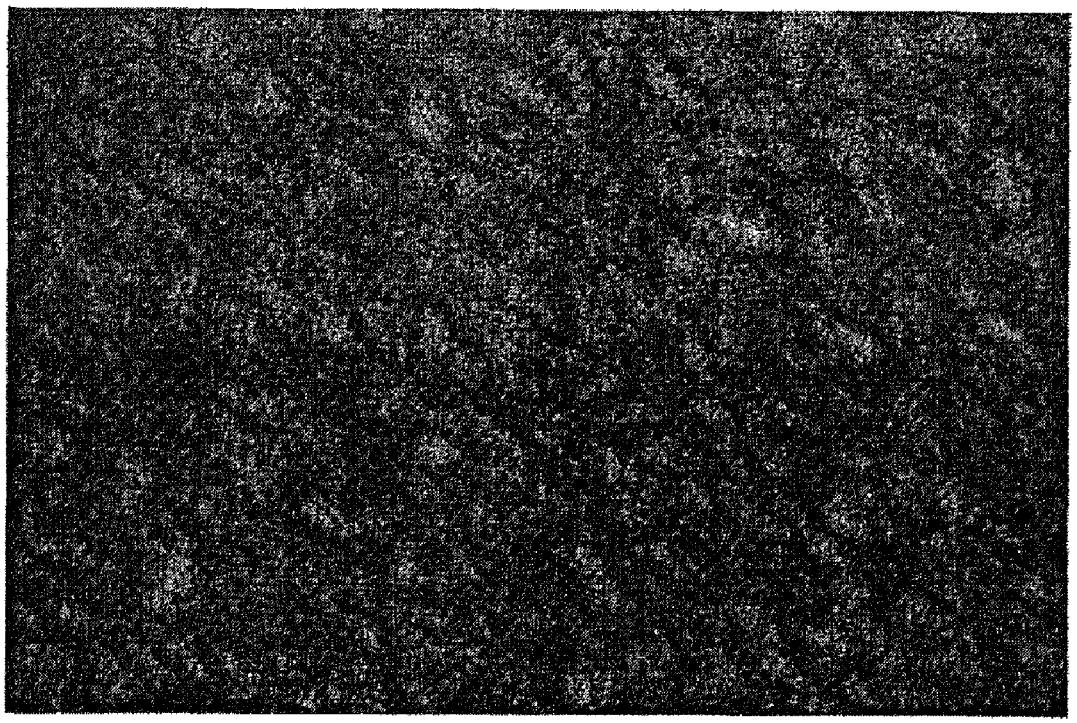
FIG. 4 is a typical speckle pattern obtained from a finger.

In accordance with this invention as exemplified in a third embodiment shown FIG. 3, a finger 10 is illuminated using a coherent laser beam 20 from a laser 30 at a selected region of the finger. The scattered rays are then collected using a camera 80 and viewed over a selected time scale. A typical speckle pattern at a given time is shown in FIG. 4.

The beat of the heart within the body, causing the blood to be pumped through the capillaries of the finger, is found to create a sound wave in the blood vessels. This pulse can be determined by monitoring the speckle pattern, which is found to change periodically with the heartbeat.

Figure 5:
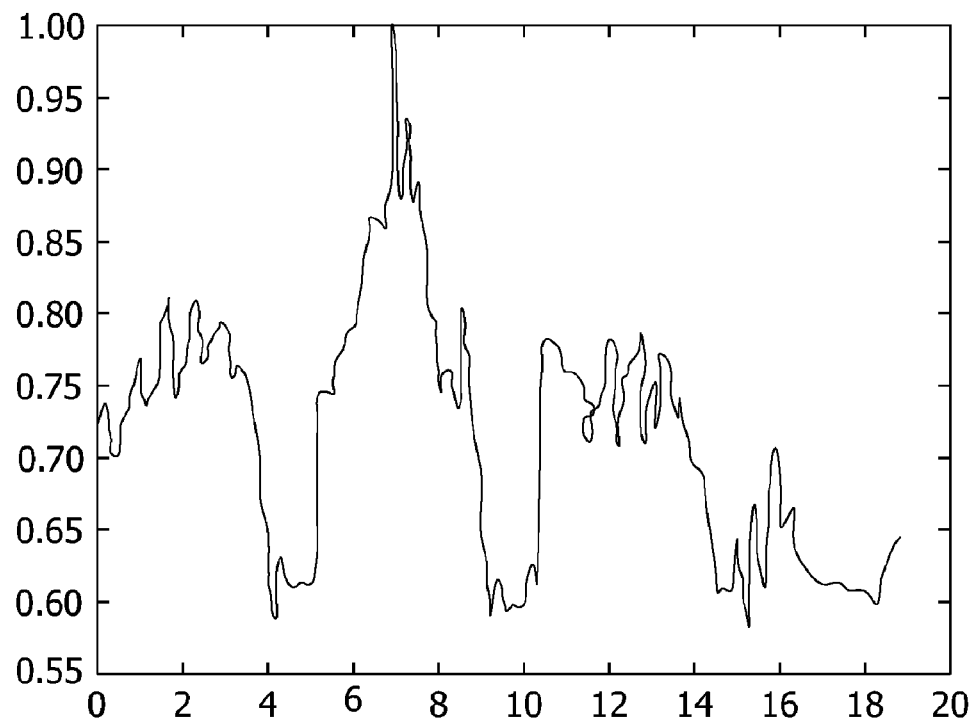
FIG. 5 is a graph representing the correlation of speckle patterns with a reference pattern.
Figure 5:
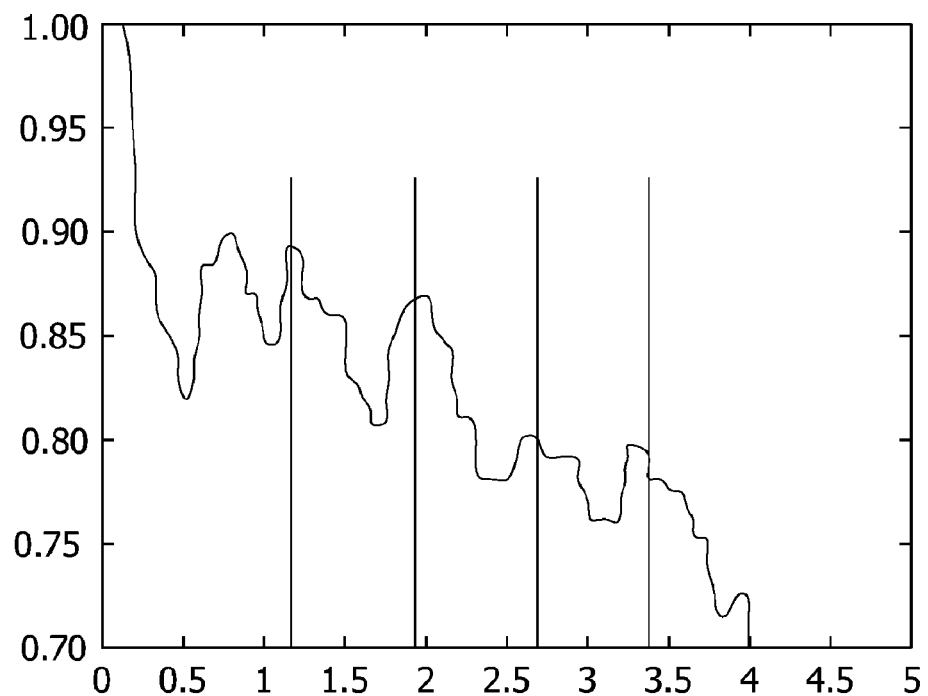

By correlating the speckle pattern obtained at one particular time frame, with a selected reference frame, for example the first and/or last, the heartbeat effect becomes clear, as shown in FIG. 5. The first plot shown in FIG. 5 gives the relative overlap agreement i.e. correlation, between the reference frame and the various frames of the speckle pattern taken over the period of 0-105 seconds. A correlation of 1 refers to two frames that are identical, whereas a correlation of 0 would imply the two frames are the inverse of each other. The second plot of FIG. 5 shows the correlation pattern over a shorter time scale. It has been found that using light with a wavelength in the blue region of the spectrum enhances the ability to monitor heartbeat using speckle investigation techniques and with this plot, the beating of the finger becomes more clear and can be used to better estimate the heartbeat rate.

Thus, interrogating a finger with an investigation system as illustrated in FIG. 1 or 3, can be used to determine the owner of the finger through analysis of the speckle pattern and/or fingerprint, as well as to distinguish between a live "beating" finger and an artificial finger, as is necessary with fingerprint security systems.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. Aspects of the invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for investigation of or ascertaining pulse or heartbeat, the method comprising the acts of:
   directing illuminating radiation to illuminate a body part, the illuminating radiation being of a wavelength or wavelength band substantially in the blue light region of the spectrum;
   imaging an optical speckle pattern of the illuminated body part, resultant from the illumination of the body part; and
   processing by a processor optical speckle pattern image data to ascertain a pulse or a heartbeat extant for the body part.

2. The method according to claim 1, wherein the optical speckle pattern is imaged using a camera, and correlations between image data from captured temporally spaced image frames are processed in order to ascertain the pulse or the heartbeat.

3. An investigation system for investigating a body part, the investigation system comprising:
   an illuminating radiation delivery arrangement, for directing illuminating radiation to the body part the illuminating radiation being of a wavelength or wavelength band substantially in the blue light region of the spectrum;
   an image capture arrangement for capturing an optical speckle pattern image of the illuminated body part, resultant from the illumination of the body part; and a processor to process image data from the image capture arrangement, wherein the image data is processed to ascertain a pulse or a heartbeat extant for the body part.

4. The investigation system according to claim 3, wherein the illumination radiation delivered is a beam of coherent light.

5. The investigation system according to claim 4, wherein the illumination radiation delivered is a beam of laser light.

6. The investigation system according to claim 3, wherein the image capture arrangement comprises a camera.

7. The investigation system according to claim 3, wherein the processor operates to use correlations between image data from captured temporally spaced image frames in order to ascertain the pulse or the heartbeat extant for the body part.

8. The investigation system according to claim 7, wherein a reference frame image data set is ascertained for the correlations, the reference frame data set comprising an average of image pixel data for a plurality of image frames.

9. An investigation system for investigating a body part, the investigation system comprising:
    an illuminating radiation delivery arrangement, for directing illuminating radiation to the body part;
    an image capture arrangement for capturing an optical speckle pattern image of the illuminated body part, resultant from the illumination of the body part;
    a processor configured to process image data from the image capture arrangement, wherein the image data is processed to compare the captured optical speckle pattern of the body part with a reference speckle pattern in order to ascertain identity for an owner of the body part, wherein the processor is further configured to process optical speckle pattern image data from the image capture arrangement to ascertain a pulse or heartbeat exhibited by the body part in order to confirm that the owner of the body part is alive.

10. The investigation arrangement according to claim 9, wherein the illumination radiation delivered is a beam of coherent light.

11. The investigation system according to claim 9, the optical speckle pattern image includes a relief image of a characteristic physical relief pattern on a surface of the body part and the processor is further configured to process the relief pattern image to ascertain the identity for the owner of the body part.

12. The investigation system according to claim 11, wherein the characteristic physical relief pattern is a fingerprint or part thereof.

13. The investigation system according to claim 9, wherein the illuminating radiation is of a wavelength or wavelength band substantially in the blue light region of the spectrum.

14. A method for investigation of a body part in order to ascertain identity for the owner of the body part, the method comprising the acts:
    directing illuminating radiation to illuminate the body part;
    imaging an optical speckle pattern of the illuminated body part, resultant from the illumination of the body part;
    processing by a processor optical speckle pattern image data to compare the optical speckle pattern of the body part with a reference speckle pattern in order to ascertain identity for an owner of the body part, including ascertaining a pulse or heartbeat exhibited by the body part in order to confirm that the owner of the body part is alive.

15. The method according to claim 14, further including the act of capturing an image of a characteristic physical relief pattern on a surface of the body part and processing image data from the captured physical relief pattern image to ascertain the identity for the owner of the body part.

16. The method according to claim 14, wherein the processing act further ascertains a reference frame image data set, the reference frame data set comprising an average of image pixel data for a plurality of image frames.

* * * * *